United States Patent
Nair et al.

(10) Patent No.: US 6,476,279 B2
(45) Date of Patent: Nov. 5, 2002

(54) METHOD OF MAKING FLUORINATED ALCOHOLS

(75) Inventors: Haridasan K. Nair, Williamsville, NY (US); Andrew Joseph Poss, Kenmore, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/759,589

(22) Filed: Jan. 12, 2001

(65) Prior Publication Data

US 2002/0095059 A1 Jul. 18, 2002

Related U.S. Application Data

(60) Provisional application No. 60/242,330, filed on Oct. 20, 2000.

(51) Int. Cl.$^7$ ................................................ C07C 31/34
(52) U.S. Cl. ................... 568/842; 568/437; 568/812; 568/814
(58) Field of Search ................... 568/812, 814, 568/437, 842

(56) References Cited

U.S. PATENT DOCUMENTS

| | | | |
|---|---|---|---|
| 3,171,861 A | * | 3/1965 | Ahlbrecht |
| 4,100,180 A | * | 7/1978 | Ichihawa |
| 4,292,452 A | * | 9/1981 | Lee |
| 4,599,358 A | | 7/1986 | Bosone et al. ............. 514/521 |
| 4,929,776 A | * | 5/1990 | Grosselin |
| 4,973,768 A | * | 11/1990 | Cordier |
| 5,654,473 A | | 8/1997 | Van Der Puy ............. 560/262 |
| 6,111,130 A | * | 8/2000 | Puy |

FOREIGN PATENT DOCUMENTS

JP  2-56462  *  2/1990

OTHER PUBLICATIONS

House, "Modern Synthetic Reactions," 2nd Ed pp. 89–94, 1972.*

E.T. McBee, Alec E. Kelley and Edward Rapkin, "Compounds Derived from 3–Halo–1,1,1–trifluoropropane" J. Am. Chem. Soc., 72, (1950), p. 5071.

H.M. Walborsky, M. Baum and D.F. Loncrini, "The Syntheses of –Trifluoromethyl Amino Acids. II. Their Microbiological Activities", J. Am. Chem. Soc., 77 (1955), pp. 3637–3640.

M. Van Der Puy, et al., "Preparation, fluorination and synthetic utility of a CFC –olefin adduct", Journal of Fluorine Chemistry, 76, (1996), pp. 44–54.

* cited by examiner

*Primary Examiner*—Michael L. Shippen
(74) *Attorney, Agent, or Firm*—Deborah Chess

(57) ABSTRACT

Disclosed are methods of producing fluorinated alcohols which find particular use in the syntheses of pharmaceutical drugs. The methods comprise generally, the steps of (a) reacting a halogenated alkane with an alkyl vinyl ether to form an unsaturated halogenated aldehyde; (b) reducing the unsaturated halogenated aldehyde to form an unsaturated halogenated alcohol; and (c) reducing the unsaturated halogenated alcohol to form a fluorinated alcohol.

28 Claims, No Drawings

METHOD OF MAKING FLUORINATED ALCOHOLS

RELATED APPLICATIONS

This application claims the benefit of U.S. Provisional Patent Application No. 60/242,330 filed Oct. 20, 2000, incorporated herein fully by reference.

FIELD OF INVENTION

The present invention relates to new methods for making fluorinated alcohols.

BACKGROUND OF THE INVENTION

Fluorinated alcohols find particular use in the syntheses of numerous pharmaceutical drug candidates. For example, 4,4,4-trifluorobutanol is used as a key intermediate in the preparation of the antiparkinson drug 3-(2-methoxyethyl)-5 [4-(4,4,4,-trifluorobutoxy)phenyl]-1,3,4,-oxadiazolo-2(3H)-one.

Applicants believe that known methods for making fluorinated alcohols are highly inefficient, often using disfavored reaction ingredients and/or reaction conditions. For example, one known prior art process for forming fluorinated alcohols comprises reacting Grignard reagents derived from 3-chloro-1,1,1-trifluoropropane with ethyl orthoformate in ether at refluxing temperatures for extended periods of time to form fluorinated aldehydes, and subsequently reducing the aldehydes to alcohols using lithium aluminum hydride. McBee et al., "Compounds Derived from 3-Halo-1,1,1-trifluoropropane", *J. Am. Chem. Soc.*, 72, p. 5071 (1950); Walborsky, H. M. et al., "The Syntheses of Trifluoromethyl Amino Acids. II. Their Microbiological Activities", *J Am. Chem. Soc.*, 77, pp. 3637–3640 (1955). Such processes are reported to have produced yields of fluorinated alcohols of only about 37% or less.

The present inventors have come to appreciate that prior art processes of the type disclosed by Walborsky, et al. are disadvantageous for several reasons. In addition to long reaction times and low yields, another disadvantage of the prior art process is that it requires reaction times and low yields, another disadvantage of the prior art process is that it requires the use of fluorinated starting materials which are not readily available and lithium aluminum hydride, which is relatively expensive. Additionally, the prior art process is disadvantageous in that it requires the use of lithium aluminum hydride in conjunction with ethereal solvents. Because lithium aluminum hydride is pyrophoric and ethereal solvents are highly flammable, there is a high risk of hazard associated with their combined use.

Recognizing these and other drawbacks of the prior art, the present inventors have perceived a need for a new, efficient and more desirable method for producing a wide range of fluorinated alcohols. These and other objects are achieved by the present invention as described below.

DESCRIPTION OF THE INVENTION AND PREFERRED EMBODIMENTS

The present invention is directed to methods of producing a wide range of fluorinated alcohols, many of which find particular use in the syntheses of pharmaceutical drug candidates. An important aspect of the invention is the discovery that fluorinated alcohols can be advantageously produced using halogenated alkanes as a principal reagent. Particularly preferred alkanes are illustrated in Formula I below:

wherein $R_F$ is a fully or partially fluorinated alkyl group and X is hydrogen or chlorine.

Applicants have discovered that halogenated alkanes can be used with great advantage in a process which comprises converting the halogenated alkane, and preferably a halogenated alkane of Formula I, to a fluorinated alcohol. Applicants have discovered that the process of the present invention is highly advantageous in at least two respects. First, the cost of producing fluorinated alcohols according to the present method is greatly reduced relative to conventional fluorinated alcohol production techniques. The lowered cost results, at least in part, because the halogenated alkanes of Formula I are readily available in commercial quantities and are relatively inexpensive, and because the present methods avoid the use of relatively expensive hydrides, such as lithium aluminum hydride, used commonly in conventional fluorinated alcohol preparation techniques. Second, the preferred form of the present conversion process involves fewer synthetic steps, and is more efficient, than known fluorinated alcohol preparation techniques.

According to preferred embodiments of the present invention, the step of converting the halogenated alkane to a fluorinated alcohol comprises the steps of: (a) reacting a halogenated alkane with an alkyl vinyl ether to form an unsaturated halogenated aldehyde; (b) reducing the unsaturated halogenated aldehyde to form an unsaturated halogenated alcohol; and (c) reducing the unsaturated halogenated alcohol to form a fluorinated alcohol.

As used herein, the term "unsaturated halogenated aldehyde" refers generally to a compound comprising an aldehyde moiety bonded to a carbon chain containing at least one carbon-carbon double bond and substituted with at least one fluorine group. An unsaturated halogenated aldehyde, for purposes of the present invention, may further comprise other substituents, including non-fluorine halogens, such as chlorine. The term "unsaturated halogenated alcohol", as used herein, refers generally to a compound comprising an alcohol moiety bonded to a carbon chain containing at least one carbon-carbon double bond and substituted with at least one fluorine group. An unsaturated halogenated alcohol, for purposes of the present invention, may further comprise other substituents, including non-fluorine halogens, such as chlorine. operation, it is believed that the methods according to the preferred aspects of the present invention involve the reaction steps shown below.

(step (a))

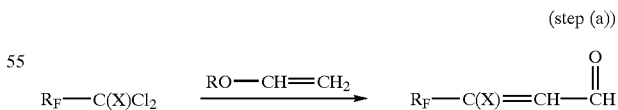

wherein $R_F$ is a fully or partially fluorinated alkyl group and X is H or Cl (step (b))

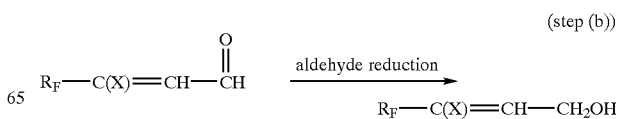

-continued

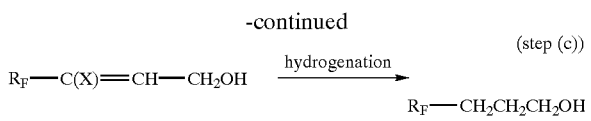
(step (c))

Reaction step (a) comprises generally reacting a halogenated alkane of Formula I with an alkyl vinyl ether to form an unsaturated halogenated aldehyde.

Examples of halogenated alkanes for use in the present invention include halogenated alkanes of Formula I wherein $R_F$ is a fully or partially fluorinated alkyl group which does not interfere with the formation of the unsaturated halogenated aldehyde. According to preferred embodiments, the halogenated alkane is a compound of Formula I wherein $R_F$ is a fully or partially fluorinated alkyl group having from about one to about ten carbons, including, for example: fluoromethyl, difluoromethyl, trifluoromethyl, fluoroethyl, difluoroethyl, trifluoroethyl, tetrafluoroethyl, pentafluoroethyl, fluoropropyl, difluoropropyl, trifluoropropyl, tetrafluoropropyl, pentafluoropropyl, hexafluoropropyl, heptafluoropropyl, as well as fluorinated derivatives of t-butyl, pentyl, hexyl, heptyl, octyl, nonyl, decyl groups and the like. In more preferred embodiments, $R_F$ is a fluorinated alkyl group having from about one to about three carbons, such as fluoromethyl, difluoromethyl, trifluoromethyl, fluoroethyl, difluoroethyl, trifluoroethyl, tetrafluoroethyl, pentafluoroethyl, fluoropropyl, difluoropropyl, trifluoropropyl, tetrafluoropropyl, pentafluoropropyl, hexafluoropropyl, heptafluoropropyl. In a particularly preferred embodiment, $R_F$ is a trifluoromethyl group. Any partially fluorinated $R_F$ groups may be further substituted with substituents which do not interfere with the formation of the unsaturated halogenated aldehyde. Examples of substituents groups which are adaptable for use in the present invention include: alkyl groups, including cyclic alkyls such as cyclohexyl; aryl groups, such as, phenyl, halogenated aryl groups; and the like.

X in a compound of Formula I may be hydrogen or chlorine. In preferred embodiments of the present invention, X is a chlorine.

A wide range of alkyl vinyl ethers may be used in the practice of the present method. Generally, any alkyl vinyl ether capable of radical addition is suitable for use in the present method. Examples of suitable alkyl vinyl ethers include compounds of Formula II:

$$R-O-C(H)=CH_2 \quad (II)$$

wherein R is an alkyl, cycloalkyl or aryl group. R as an alkyl group may be a group having from about one to about twelve carbons such as a methyl, ethyl, propyl, isopropyl, butyl, tert-butyl, pentyl, hexyl, heptyl, octyl, nonyl, decyl, undecyl, dodecyl and the like. Preferred alkyl groups include those having from about one to about six carbons such as methyl, ethyl, propyl, isopropyl, butyl, tert-butyl, pentyl and hexyl. R as a cycloalkyl group may be a group having from about five to about twelve carbons including, for example, cyclopentyl, cyclohexyl, cycloheptyl, cyclooctyl, cyclononyl, cyclodecyl, cycloundecyl, cyclododecyl and the like. R as an aryl group may be a group having from about six to about twelve carbons including, for example, phenyl, napthyl and the like. In addition, R as an alkyl, cycloalkyl or aryl group may be substituted with any substitution group which does not interfere with the reaction of the alkyl vinyl ether with a halogenated alkane to form a halogenated unsaturated aldehyde.

Preferably, the alkyl vinyl ethers used in the present invention are compounds of Formula II wherein R is a an alkyl group having from about two to about six carbons such as ethyl, propyl, isopropyl, butyl, tert-butyl, pentyl, hexyl groups and the like. In even more preferred embodiments, the alkyl vinyl ether is a compound of Formula II wherein R is a tert-butyl group.

Those skilled in the art will appreciate that the amounts of halogenated alkane and alkyl vinyl ether to be used according to the present invention will depend on many variables, including the particular alkane and ether being used and the desired yield from the reaction. Preferably, the amount of reagents used is an amount effective to achieve a greater than 25% conversion of the halogenated alkane starting material to an unsaturated halogenated aldehyde. For example, in certain preferred processes in which the halogenated alkane is $CF_3CCl_3$ and the alkyl vinyl ether is tert-butyl vinyl ether, the mole ratio of alkane to ether is preferably from about 8:1 to about 1:1, more preferably from about 6:1 to about 1.5:1 and even more preferably from about 4:1 to about 2:1.

Although applicants do not wish to be bound by or to any theory of operation, it is believed that, in many embodiments, the formation of an unsaturated halogenated aldehyde from a halogenated alkane according to the present invention involves a free-radical process. Accordingly, in many embodiments, the reaction step (a) involves the use of radical reaction promoters.

A wide range of radical reaction promoters can be used in the practice of the present invention including, for example, ultraviolet ("UV") light. It is well-known in the art to use UV light to promote free-radical processes and those of skill in the art will be readily able to adapt conventional methods of UV irradiation to the present invention without undue experimentation. For example, in preferred embodiments, a sample comprising a halogenated alkane of the present invention and an alkyl vinyl ether is irradiated using a medium-pressure mercury UV lamp at a wavelength of from about 200 to about 400 nanometers.

Other radical reaction promoters suitable for use in the present invention include peroxides or transition metal salts, such as iron or copper salts, in the presence of primary amines, secondary amines or azo-derivatives as disclosed in U.S. Pat. No. 4,599,358.

Those skilled in the art will appreciate that the conditions under which the step (a) reaction occurs, including the temperature and period of reaction, will depend on numerous factors, including the particular starting reagents used and the desired reaction yield. In view of the teachings contained herein, those skilled in the art will be able to select the appropriate reaction conditions to achieve the particular desired result. For preferred embodiments in which the halogenated alkane reactant is $CF_3CCl_3$ and the alkyl vinyl ether is tert-butyl vinyl ether, the reaction step (a) is preferably carried out at temperatures from about 0° C. to about 200° C., more preferably from about 25° C. to about 100° C., and even more preferably from about 35° C. to about 45° C. For such embodiments, the reaction time is preferably from about 1 to about 6 hours, more preferably from about 1 to about 4 hours, and even more preferably from about 1 to about 2 hours.

In many embodiments, the unsaturated aldehyde produced in step (a) will comprise both E and Z isomers. However, in preferred embodiments, the E isomer is formed predominantly. For example, in preferred embodiments of the present invention, wherein the halogenated alkane reactant is $CF_3CCl_3$ and the alkyl vinyl ether is tert-butyl vinyl ether, the E isomer of the resulting aldehyde is formed in amounts greater than about 98 wt. % (based on total weight of E and Z aldehyde formed).

The unsaturated aldehydes formed in step (a) can be removed from the reaction product via a wide range conventional methods including, particularly, fractional distillation.

Reduction step (b) comprises generally reducing the unsaturated halogenated aldehyde to an unsaturated halogenated alcohol, preferably using a reducing agent.

Reducing agents suitable for use in the present invention may include any compounds which enhance the conversion of an unsaturated halogenated aldehyde to an unsaturated halogenated alcohol. Examples of reducing agents suitable for use in the present invention include elemental hydrogen and metal hydrides, such as sodium borohydride, lithium borohydride, and the like. Other metal hydrides, such as lithium aluminum hydride, are suitable for use in the present invention but are disfavored due to the increased cost associated with such hydrides. Particularly preferred reducing agents are sodium borohydride and lithium borohydride.

Generally, the reduction step (b) is conducted in a reaction solvent. Suitable reactions solvents include: alcohols, such as methanol, ethanol, and the like; acids, such as, glacial acetic acid and the like; and ethers, such as, diethyl ether, diglyme, tetrahydrofuran ("THF"), and the like. In preferred embodiments, the solvent comprises glacial acetic acid or THF.

A wide range of temperature, time, and pressure conditions for aldehyde reduction reactions using metal hydrides are known. The particular set of reaction conditions used in any given reaction will depend on the particular reactants and reducing agent used and the time and yield of product desired. Speaking generally, it is believed that the temperature of reaction will range from about −78° C. to about 25° C. Preferably, the temperature of reaction will be from about −15° C. to about 20° C., and more preferably from about 0° C. to about 15° C. In embodiments wherein the aldehyde comprises 3-chloro-4,4,4-trifluorobut-2-enal and the reducing agent comprises sodium borohydride, the reaction time is preferably from about 1 to about 6 hours, more preferably from about 1 to about 4 hours, and even more preferably from about 1 to about 6 hours.

The unsaturated alcohol product formed from the reduction step (b) of the present invention may be purified by conventional methods such as: filtering, washing, drying, concentrating under reduced pressure, and the like.

Reduction step (c) of the present invention generally comprises reacting the unsaturated halogenated alcohol with hydrogen in the presence of a reduction catalyst to form a fluorinated alcohol. Preferably, the reaction is carried out in a pressure reaction vessel, such as a hard glass reactor or an autoclave, especially a glass or teflon-lined autoclave. In general suitable sources of hydrogen for the reduction reaction include any material capable of providing hydrogen to the reaction. A preferred source of hydrogen is elemental hydrogen.

A wide range of reduction catalysts for use in the present invention are known. As used herein, the term "reduction catalyst" refers generally to an inorganic metal catalyst which promotes a reaction involving the conversion of an unsaturated double bond to a saturated carbon moiety. Such reduction catalysts include, for example, Rainey Nickel, oxides, hydroxides, halides, oxyhalides and inorganic salts of metals, not limited to, platinum, palladium, nickel and ruthenium, as well as, supported metal catalysts, such as, platinum or palladium on activated carbon. Preferred reduction catalysts include platinum or palladium on activated carbon.

With respect to the preferred reduction catalysts, any suitable amount of catalyst can be associated with the activated carbon carrier, typically the amount being related to the particular catalyst used. It is believed that the most widely used amounts of catalyst will fall within the range of about 0.1 to about 70 wt. % of catalyst based on the total weight of catalyst and carrier. A particularly preferred metal/activated carbon catalyst comprises 5% platinum or palladium on carbon.

In addition to the unsaturated halogenated alcohol and the reduction catalyst, the reaction mixture can include other materials of the type used in known hydrogenation reduction reactions. For example, in certain preferred embodiments, the reaction mixture can include a base and/or a solvent. The particular base or solvent chosen for use in any particular reaction will depend on the nature of the reactants and conditions of reactions. Examples of bases suitable for use in the present invention include metal acetates, such as, potassium acetate, sodium acetate, ammonium acetate and the like. Preferred bases include metal acetates such as sodium acetate or potassium acetate.

Examples of solvents suitable for use in the present invention include: alcohols, such as methanol, ethanol and the like; and esters, such as, ethylacetate and the like. In certain preferred embodiments of the present invention, the solvent is methanol.

The temperature and pressure at which the reaction is conducted and the period of reaction will depend on the starting materials and amounts used. In view of the present teachings, those skilled in the art will be able to adapt the reaction parameters to achieve the particular desired results for numerous starting materials and desired fluorinated alcohols. For methods involving the use of 3-chloro-4,4,4-trifluorobut-2-en-1-ol as the unsaturated alcohol, temperatures in the reduction reactor are preferably from about 10° C. to about 100° C., more preferably from about 25° C. to about 80° C., and even more preferably from about 40° C. to about 60° C. For such embodiments, the reactor pressure is preferably from about 10 to about 200 psi, more preferably from about 20 to about 100 psi, and even more preferably from about 30 to about 50 psi. For such embodiments, the reactor time is preferably from about 1 to about 30 hours, more preferably from about 6 to about 20 hours, and even more preferably from about 12 to about 16 hours.

The product formed from the reduction step (c) of the present invention may be purified by conventional methods such as: filtering, washing, drying, concentrating under reduced pressure, distillation and the like.

EXAMPLES

In order to illustrate, in a non-limiting manner, the present invention is described in connection with the following examples.

Example 1

This example illustrates the preparation of 3-chloro-4,4,4-trifluorobut-2-enal from 1,1,-trifluoro-2,2,2-trichloroethane.

A mixture of 1,1,1-trifluoro-2,2,2-trichloroethane and tert-butylvinyl ether in a 3:1 molar ratio is introduced to a jacketed photochemical reaction vessel. The mixture is irradiated using a medium-pressure mercury UV lamp so as to maintain the temperature of the mixture at about 35–45° C. for about 2 hours. The resultant reaction mixture is concentrated to remove volatiles and distilled to produce 3-chloro-4,4,4-trifluorobut-2-enal in a 60% yield.

Example 2

This example illustrates the preparation of 3-chloro-4,4,4-trifluorobut-2-en-1-ol from 3-chloro-4,4,4-trifluorobut-2-enal using glacial acetic acid as a reaction solvent.

A reaction mixture of 3-chloro-4,4,4-trifluorobut-2-enal (75 g, 0.47 mol) and glacial acetic acid (200 mL) is introduced to a 500 mL round-bottomed reaction flask equipped with an addition funnel and a condenser. The flask, including the reaction mixture contained therein, is immersed in an ice bath, and sodium borohydride (17.7 g, 0.47 mol) is added slowly via a solid addition funnel under purge of nitrogen. Upon addition of the sodium borohydride, a rapid exotherm with frothing occurs. After complete addition of the sodium borohydride, the reaction mixture is allowed to equillibrate to room temperature and is stirred for an hour. The reaction mixture is then poured into cold water (400 mL) with mixing and extracted with diethyl ether (2×200 mL). The ether extract is washed with saturated sodium bicarbonate solution until the solution pH is neutral, filtered, dried using magnesium sulfate and concentrated to afford 73g (96% yield) of 3-chloro-4,4,4-trifluorobut-2-en-1-ol as a clear liquid. This material is used for the next step, as described in Example 4, without further purification.

Example 3

This example illustrates the preparation of 3-chloro-4,4,4-trifluorobut-2-en-1-ol from 3-chloro-4,4,4-trifluorobut-2-enal using THF as a reaction solvent.

A mixture of 3-chloro-4,4,4-trifluorobut-2-enal (10 g, 0.063 mol) and THF (30 mL) is introduced to a 100 mL round-bottomed reaction flask equipped with an addition funnel and a condenser under nitrogen purge. The flask, including the reaction mixture contained therein, is immersed in a water bath, and sodium borohydride (1.2 g, 0.032 mol) is added slowly, under purge of nitrogen, via a solid addition funnel such that the reaction mixture does hot rise above 45° C. After complete addition of the sodium borohydride, the reaction mixture is stirred at ambient temperature for one hour. The reaction mixture is then poured into cold water (30 mL) with mixing and extracted with diethyl ether (2×40 mL). The ether extract is dried using magnesium sulfate, filtered and concentrated to afford 10.1 g(quantitative yield) of 3-chloro-4,4,4-trifluorobut-2-en-l-ol as a clear liquid.

Example 4

This example illustrates the preparation of 4,4,4-trifluorobutan-1-ol from 3-chloro-4,4,4-trifluorobut-2-en1-ol.

A mixture of 3-chloro-4,4,4-trifluorobut-2-en-1-ol (72 g, 0.42 mol), 5% palladium on activated carbon (240 mg), potassium acetate (41.2 g, 0.42 mol) and methanol (100 mL) is introduced to a 500 mL hard glass tube reactor under a nitrogen purge. The reactor is evacuated partially and pressurized with hydrogen to 45 psi. The reaction mixture is then heated at 55–60° C. for about 12 to about 16 hours. The reactor is cooled to room temperature (25° C.) and excess hydrogen gas is vented. The reaction mixture is filtered and the resulting filtrate is added to water, extracted with ether (3×200 mL) and washed with sodium bicarbonate solution until the reaction solution has a neutral pH. The solution is dried with magnesium sulfate, filtered, concentrated and distilled to afford 4,4,4-trifluorobutan-1-ol in 60% yield.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for the preparation of fluorinated alcohol compounds comprising the steps of:
   (a) reacting a halogenated alkane having at least one fluorine substituent with an ether reactant selected from the group consisting of alkyl vinyl ethers, cycloalkyl vinyl ethers, aryl vinyl ethers, and combinations of two or more thereof, to form a halogenated unsaturated aldehyde;
   (b) reducing said halogenated unsaturated aldehyde to form a halogenated unsaturated alcohol; and
   (c) reducing said halogenated unsaturated alcohol to form a fluorinated alcohol.

2. The method of claim 1, wherein said halogenated alkane comprises a compound of the formula:

$$R_F\text{—}C(X)\text{—}Cl_2$$

wherein $R_F$ is a fully or partially fluorinated alkyl group and X is H or Cl.

3. The method of claim 2, wherein $R_F$ is a fully or partially fluorinated alkyl group comprising 1 to 10 carbon atoms.

4. The method of claim 3, wherein $R_F$ is a fully or partially fluorinated alkyl group comprising 1 to 3 carbon atoms.

5. The method of claim 3 wherein $R_F$ is a substituted fluorinated alkyl group.

6. The method of claim 4, wherein $R_F$ is trifluoromethyl.

7. The method of claim 6, wherein X is a chlorine.

8. The method of claim 7, wherein R is an alkyl group comprising 1 to 12 carbon atoms.

9. The method of claim 1, wherein said ether reactant comprises a compound of the formula:

$$R\text{—}O\text{—}C(H)\text{=}CH_2$$

wherein R is an unsubstituted alkyl, a substituted alkyl, an unsubstituted cycloalkyl, a substituted cycloalkyl, an unsubstituted aryl, a substituted aryl, or combinations of two or more of these.

10. The method of claim 8, wherein R is a tert-butyl group.

11. The method of claim 1, wherein said reacting step (a) comprises reacting said halogenated alkane with said ether reactant in the presence of a radical reaction promoter.

12. The method of claim 11, said radical reaction promoter comprises ultraviolet light.

13. The method of claim 1, wherein said reaction step (a) comprises reacting said halogenated alkane with said ether reactant at a temperature of from about 0° C. to about 200° C.

14. The method of claim 13, wherein said reaction step (a) comprises reacting said halogenated alkane with said ether reactant at a temperature of from about 35° C. to about 45° C.

15. The method of claim 1, wherein said reduction step (b) comprises reducing said halogenated unsaturated aldehyde in the presence of a reducing agent.

16. The method of claim 15, wherein said reducing agent comprises a metal hydride.

17. The method of claim 16, wherein said metal hydride is selected from the group consisting of sodium borohydride, lithium borohydride and mixtures thereof.

18. The method of claim 15, wherein said reduction step (b) further comprises reducing said halogenated unsaturated aldehyde in the presence of a reaction solvent.

19. The method of claim 18, wherein said reaction solvent is selected from the group consisting of glacial acetic acid, diethyl ether, diglyme, THF, methanol, ethanol and combinations of two or more of these.

20. The method of claim 1, wherein said reduction step (c) comprises reacting said unsaturated halogenated alcohol with hydrogen in the presence of a reducing catalyst.

21. The method of claim 20, wherein said reducing catalyst is selected from the group consisting of platinum oxides, platinum hydroxides, platinum halides, platinum oxyhalides, inorganic platinum salts, palladium oxides, palladium hydroxides, palladium halides, palladium oxyhalides, inorganic palladium salts, nickel oxides, nickel hydroxides, nickel halides, nickel oxyhalides, inorganic nickel salts, ruthenium oxides, ruthenium hydroxides, ruthenium halides, ruthenium oxyhalides, inorganic ruthenium salts, platinum on activated carbon, palladium on activated carbon and combinations of two or more of these.

22. The method of claim 21, wherein said reducing catalyst is selected from the group consisting of platinum on activated carbon, palladium on activated carbon and combinations of two or more of these.

23. The method of claim 20, wherein said reduction step (c) is conducted in the presence of a base.

24. The method of claim 23, wherein said base comprises a metal acetate.

25. The method of claim 24, wherein said metal acetate is selected from the group consisting of sodium acetate, potassium acetate and combinations of two or more of these.

26. The method of claim 23, wherein said reduction step (c) comprises reacting said unsaturated halogenated alcohol with hydrogen in the presence of a reaction solvent.

27. The method of claim 26, wherein said reaction solvent is selected from the group consisting of methanol, ethylacetate and combinations of two or more of these.

28. The method of claim 1, wherein said fluorinated alcohol consists essentially of 4,4,4-trifluorobutan-1-ol and, said reacting step (a) comprises reacting 1,1,1-trifluoro-2,2,2-trichloroethane with tert-butylvinyl ether to form 3-chloro-4,4,4-trifluorobut-2-enal, said reducing step (b) comprises reducing said 3-chloro-4,4,4-trifluorobut-2-enal to produce 3-chloro-4,4,4-trifluorobut-2-en-1-ol, said reducing step (c) comprises reducing said 3-chloro-4,4,4-trifluorobut-2-en-1-ol to produce 4,4,4-trifluorobutan-1-ol.

* * * * *